United States Patent
Abunassar et al.

(10) Patent No.: US 11,065,119 B2
(45) Date of Patent: Jul. 20, 2021

(54) LONG ARM VALVE REPAIR CLIP

(71) Applicant: EVALVE, INC., Santa Clara, CA (US)

(72) Inventors: Chad Abunassar, San Francisco, CA (US); Jessie Garcia, Newark, CA (US); Tamer Mahmoud, Sunnyvale, CA (US); Brandon Chu, San Francisco, CA (US); Santosh Prabhu, Sunnyvale, CA (US)

(73) Assignee: Evalve, Inc., Santa Clara, CA (US)

( * ) Notice: Subject to any disclaimer, the term of this patent is extended or adjusted under 35 U.S.C. 154(b) by 301 days.

(21) Appl. No.: 15/977,995

(22) Filed: May 11, 2018

(65) Prior Publication Data
US 2018/0325671 A1   Nov. 15, 2018

Related U.S. Application Data

(60) Provisional application No. 62/505,810, filed on May 12, 2017.

(51) Int. Cl.
*A61F 2/24*   (2006.01)
*A61B 17/29*   (2006.01)
(Continued)

(52) U.S. Cl.
CPC ...... *A61F 2/2466* (2013.01); *A61B 17/00234* (2013.01); *A61B 17/08* (2013.01);
(Continued)

(58) Field of Classification Search
CPC .............. A61B 17/00; A61B 17/00234; A61B 17/0469; A61B 17/3468;
(Continued)

(56) References Cited

U.S. PATENT DOCUMENTS 2,097,018 A   10/1937   Chamberlain
2,108,206 A   2/1938   Meeker
(Continued)

FOREIGN PATENT DOCUMENTS

DE   3504292 C1   7/1986
DE   101 16 168 A1   11/2001
(Continued)

OTHER PUBLICATIONS

Abe et al., "De Vega's Annuloplasty for Acquired Tricuspid Disease: Early and Late Results in 110 Patients," Ann. Thorac. Surg. 62:1876-1877 (1996).
(Continued)

*Primary Examiner* — George J Ulsh
(74) *Attorney, Agent, or Firm* — Baker Botts L.L.P.

(57) ABSTRACT

Fixation device for engaging tissue including a pair of fixation elements, each fixation element has a first end and a second end opposite the first end, the first ends are moveable between a closed position and an open position. The fixation device further includes a pair of gripping elements. Each gripping element is moveable with a respective fixation element and disposed in opposition to at least a portion of the respective fixation element to capture tissue therebetween. The fixation device further includes a central portion operatively connected to each gripping element at a respective central portion-gripping element interface. The central portion has at least one distal end and a width "$W_1$" proximate the distal end. Each of the gripping elements has a free end opposite its respective central portion-gripping element interface and a length "$L_1$" defined between the respective central portion-gripping element interface and the free end. The length $L_1$ fixation elements is at least about three times the width $W_1$.

21 Claims, 15 Drawing Sheets

(51) Int. Cl.
- *A61B 17/00* (2006.01)
- *A61B 17/08* (2006.01)
- *A61B 17/04* (2006.01)
- *A61B 17/128* (2006.01)

(52) U.S. Cl.
CPC ........ *A61B 17/29* (2013.01); *A61B 17/0469* (2013.01); *A61B 17/1285* (2013.01); *A61B 2017/00243* (2013.01); *A61F 2220/0016* (2013.01)

(58) Field of Classification Search
CPC ........ A61B 2017/00243; A61B 2017/00557; A61B 2017/00783; A61B 2017/00867; A61B 2017/0401; A61B 2017/0464; A61F 2210/0014; A61F 2/2466; A61F 2/24; A61F 2220/0025; A61F 2220/0041; A61F 2/2418; A61F 2230/0013; A61F 2/243; A61F 2230/0004; A61F 2/2442; A61F 2/2445; A61F 2/2457; A61F 2/246; A61F 2/2427; A61F 2/2454; A61F 2/2463; A61F 2210/009; A61F 2220/0008; A61F 2220/0075; A61F 2220/0091; A61F 2230/0008; A61F 2230/0045; A61F 2230/0069; A61F 2230/0093; A61F 2240/00; A61F 2250/0036; A61F 2250/006; A61F 2250/0069; A61L 27/04

See application file for complete search history.

(56) References Cited

U.S. PATENT DOCUMENTS

| | | |
|---|---|---|
| 3,296,668 A | 1/1967 | Aiken |
| 3,378,010 A | 4/1968 | Codling et al. |
| 3,557,780 A | 1/1971 | Sato |
| 3,671,979 A | 6/1972 | Moulopoulos |
| 3,675,639 A | 7/1972 | Cimber |
| 3,874,338 A | 4/1975 | Happel |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,458,682 A | 7/1984 | Cerwin |
| 4,425,908 A | 11/1984 | Simon |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Kreuter et al. |
| 5,368,564 A | 11/1994 | Savage |
| 5,368,601 A | 11/1994 | Sauer et al. |
| 5,383,886 A | 1/1995 | Kensey et al. |
| 5,391,182 A | 2/1995 | Chin |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |

(56) References Cited

U.S. PATENT DOCUMENTS

| | | |
|---|---|---|
| 5,620,461 A | 4/1997 | Muijs Van De Moer et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |

(56) References Cited

U.S. PATENT DOCUMENTS

| | | |
|---|---|---|
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,736,388 B2 | 6/2010 | Goldfarb et al. |
| 7,811,296 B2 | 10/2010 | Goldfarb et al. |
| 8,057,493 B2 | 11/2011 | Goldfarb et al. |
| 8,303,608 B2 | 11/2012 | Goldfarb et al. |
| 8,500,761 B2 | 8/2013 | Goldfarb et al. |
| 8,734,505 B2 | 5/2014 | Goldfarb et al. |
| 8,740,920 B2 | 6/2014 | Goldfarb et al. |
| 9,510,829 B2 | 12/2016 | Goldfarb et al. |
| 9,572,666 B2 | 2/2017 | Basude et al. |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |

(56) References Cited

U.S. PATENT DOCUMENTS

| | | |
|---|---|---|
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2007/0038293 A1 | 2/2007 | St. Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0197858 A1 | 8/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2013/0066342 A1 | 3/2013 | Dell et al. |
| 2014/0249553 A1 | 9/2014 | Kimura et al. |
| 2017/0020521 A1 | 1/2017 | Krone et al. |
| 2017/0042546 A1 | 2/2017 | Goldfarb et al. |
| 2017/0239048 A1 | 8/2017 | Goldfarb et al. |

FOREIGN PATENT DOCUMENTS

| | | |
|---|---|---|
| EP | 0 179 562 B1 | 7/1989 |
| EP | 0 558 031 B1 | 2/1993 |
| EP | 0 684 012 A2 | 11/1995 |
| EP | 0 727 239 A2 | 8/1996 |
| EP | 0 782 836 A1 | 7/1997 |
| EP | 1 230 899 A1 | 8/2002 |
| EP | 1 674 040 A2 | 6/2006 |
| FR | 2 768 324 A1 | 3/1999 |
| GB | 1 598 111 A | 9/1981 |
| GB | 2 151 142 A | 7/1985 |
| JP | 09-253030 A | 9/1997 |
| JP | 11-089937 A | 4/1999 |
| JP | 2000-283130 A | 10/2000 |
| JP | 2015-502548 A | 1/2015 |
| WO | WO 81/00668 A1 | 3/1981 |
| WO | WO 91/01689 A1 | 2/1991 |
| WO | WO 91/18881 A1 | 12/1991 |
| WO | WO 92/12690 A1 | 8/1992 |
| WO | WO 94/18881 A1 | 9/1994 |
| WO | WO 94/18893 A1 | 9/1994 |
| WO | WO 95/11620 A2 | 5/1995 |
| WO | WO 95/15715 A1 | 6/1995 |
| WO | WO 96/14032 A1 | 5/1996 |
| WO | WO 96/20655 A1 | 7/1996 |
| WO | WO 96/22735 A1 | 8/1996 |
| WO | WO 96/30072 A1 | 10/1996 |
| WO | WO 97/18746 A2 | 5/1997 |
| WO | WO 97/25927 A1 | 7/1997 |
| WO | WO 97/26034 A1 | 7/1997 |
| WO | WO 97/38748 A2 | 10/1997 |
| WO | WO 97/39688 A2 | 10/1997 |
| WO | WO 97/48436 A2 | 12/1997 |
| WO | WO 98/07375 A1 | 2/1998 |
| WO | WO 98/24372 A1 | 6/1998 |
| WO | WO 98/30153 A1 | 7/1998 |
| WO | WO 98/32382 A1 | 7/1998 |
| WO | WO 98/35638 A1 | 8/1998 |
| WO | WO 99/00059 A1 | 1/1999 |
| WO | WO 99/01377 A1 | 1/1999 |
| WO | WO 99/07354 A2 | 2/1999 |
| WO | WO 99/13777 A1 | 3/1999 |
| WO | WO 99/66967 A1 | 12/1999 |
| WO | WO 00/02489 A1 | 1/2000 |
| WO | WO 00/03651 A1 | 1/2000 |
| WO | WO 00/03759 A2 | 1/2000 |
| WO | WO 00/12168 A1 | 3/2000 |
| WO | WO 00/44313 A1 | 8/2000 |
| WO | WO 00/59382 A1 | 10/2000 |
| WO | WO 00/60995 A2 | 10/2000 |
| WO | WO 01/00111 A1 | 1/2001 |
| WO | WO 01/00114 A1 | 1/2001 |
| WO | WO 01/03651 A2 | 1/2001 |
| WO | WO 01/26557 A1 | 4/2001 |
| WO | WO 01/26586 A1 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 A1 | 4/2001 |
| WO | WO 01/28455 A1 | 4/2001 |
| WO | WO 01/47438 A1 | 7/2001 |
| WO | WO 01/49213 A2 | 7/2001 |
| WO | WO 01/50985 A1 | 7/2001 |
| WO | WO 01/54618 A1 | 8/2001 |
| WO | WO 01/56512 A1 | 8/2001 |
| WO | WO 01/66001 A2 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 A1 | 1/2002 |

(56) References Cited

FOREIGN PATENT DOCUMENTS

| WO | WO 02/34167 A2 | 5/2002 |
|---|---|---|
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 A2 | 1/2003 |
| WO | WO 03/003930 A1 | 1/2003 |
| WO | WO 03/020179 A1 | 3/2003 |
| WO | WO 03/028558 A2 | 4/2003 |
| WO | WO 03/037171 A2 | 5/2003 |
| WO | WO 03/047467 A1 | 6/2003 |
| WO | WO 03/049619 A2 | 6/2003 |
| WO | WO 03/073910 A2 | 9/2003 |
| WO | WO 03/073913 A2 | 9/2003 |
| WO | WO 03/082129 A2 | 10/2003 |
| WO | WO 03/105667 A2 | 12/2003 |
| WO | WO 2004/004607 A1 | 1/2004 |
| WO | WO 2004/012583 A2 | 2/2004 |
| WO | WO 2004/012789 A2 | 2/2004 |
| WO | WO 2004/014282 A2 | 2/2004 |
| WO | WO 2004/019811 A2 | 3/2004 |
| WO | WO 2004/030570 A2 | 4/2004 |
| WO | WO 2004/037317 A2 | 5/2004 |
| WO | WO 2004/045370 A2 | 6/2004 |
| WO | WO 2004/045378 A2 | 6/2004 |
| WO | WO 2004/045463 A2 | 6/2004 |
| WO | WO 2004/047679 A1 | 6/2004 |
| WO | WO 2004/062725 A1 | 7/2004 |
| WO | WO 2004/082523 A2 | 9/2004 |
| WO | WO 2004/082538 A2 | 9/2004 |
| WO | WO 2004/093730 A2 | 11/2004 |
| WO | WO 2004/103162 A2 | 12/2004 |
| WO | WO 2004/112585 A2 | 12/2004 |
| WO | WO 2004/112651 A2 | 12/2004 |
| WO | WO 2005/002424 A2 | 1/2005 |
| WO | WO 2005/018507 A2 | 3/2005 |
| WO | WO 2005/027797 A1 | 3/2005 |
| WO | WO 2005/032421 A2 | 4/2005 |
| WO | WO 2005/062931 A2 | 7/2005 |
| WO | WO 2005/112792 A2 | 12/2005 |
| WO | WO 2006/037073 A2 | 4/2006 |
| WO | WO 2006/105008 A1 | 10/2006 |
| WO | WO 2006/105009 A1 | 10/2006 |
| WO | WO 2006/115875 A2 | 11/2006 |
| WO | WO 2006/115876 A2 | 11/2006 |

OTHER PUBLICATIONS

Abe et al., "De Vega's Annuloplasty for Acquired Tricuspid Disease: Early and Late Results in 110 Patients," Ann. Thorac. Surg., 48:670-676 (1989).
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The edge to edge technique," The European Association for Cardio-Thoracic Surgery 14th Annual Meeting, Oct. 7-11, 2000, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Alvarez et al., "Repairing the Degenerative Mitral Valve: Ten to Fifteen-year Followup," J. Thorac. Cardiovasc. Surg., 112:238-247 (1996).
Arisi et al., "Mitral Valve Repair with Alfieri Technique in Mitral Regurgitation of Diverse Etiology: Early Echocardiographic Results," Circulation Supplement II, 104(17):3240 (2001).

Bach et al., "Early Improvement in Congestive Heart Failure After Correction of Secondary Mitral Regurgitation in End-stage Cardiomyopathy," Am. Heart J., 129:1165-1170 (1995).
Bach et al., "Improvement Following Correction of Secondary Mitral Regurgitation in End-stage Cardiomyopathy with Mitral Annuloplasty," Am. J. Cardiol., 78:966-969 (1996).
Bailey, "Mitral Regurgitation" in Surgery of the Heart, Chapter 20, pp. 686-737 (1955).
Bernal et al., "The Valve Racket': a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Bolling et al., "Surgery for Acquired Heart Disease: Early Outcome of Mitral Valve Reconstruction in Patients with End-stage Cardiomyopathy," J. Thor. And Cariovasc. Surg., Apr. 1995, pp. 676-683, vol. 109.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dec et al., "Idiopathic Dilated Cardiomyopathy," N. Engl. J. Med., 331:1564-1575 (1994).
Derwent citing German language patent, EP 684012 published Nov. 12, 1995, for: "Thread for constructing surgical seam—has flexible section with two ends, with lower fastening part on thread first end having hollow cylinder with continuous hole through which surgical needle threads".
Derwent citing Japanese language patent, JP 11089937 published Jun 4, 1999, for: "Catheter for mitral regurgitation test—includes jet nozzles provided on rear side of large diametered spindle shaped portion attached to end of narrow diametered tube".
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].
Fucci et al., "Improved Results with Mitral Valve Repair Using New Surgical Techniques," Eur. J. Cardiothorac. Surg., 9:621-627 (1995).
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).

(56) References Cited

OTHER PUBLICATIONS

Gateliene, "Early and postoperative results results of metal and tricuspid valve insufficiency surgical treatment using edge-to-edge central coaptation procedure," (Oct. 2002) 38 (Suppl 2):172-175.
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
International Search Report dated Aug. 29, 2018 in International Application No. PCT/US2018/032446.
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kameda et al., "Annuloplasty for Severe Mitral Regurgitation Due to Dilated Cardiomyopathy," Ann. Thorac. Surg., 61:1829-1832 (1996).
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade Atrial Septostomy: Experience with the First 50 Procedures," Cathet. Cardiovasc. Diagn., 23:257-262 (1991).
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. Of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The Edge-to-edge Technique: A Simplified Method to Correct Mitral Insufficiency," Eur. J. Cardiothorac. Surg., 13:240-246 (1998).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
McCarthy et al., "Tricuspid Valve Repair with the Cosgrove-Edwards Annuloplasty System," Ann. Thorac. Surg., 64:267-268 (1997).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37:263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. 41-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al, "Clinical Use of Blade Atrial Septostomy," Circulation, 58:600-608 (1978).
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al., "Linear Segmental Annuloplasty for Mitral Valve Repair," Ann. Thorac. Surg., 63:1805-1806 (1996).
Robicsek et al., #60 The Bicuspid Aortic Valve: How Does It Function? Why Does It Fail? 2003 STS Presentation, [Abstract Only].
Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al., "Long-Term Follow-Up of Rheumatic Patients Undergoing Left-Sided Valve Replacement with Tricuspid Annuloplasty—Validity of Preoperative Echocardiographic Criteria in the Decision to Perform Tricuspid Annuloplasty," Am. J. Cardiol., 81:1013-1016 (1998).
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).

(56) References Cited

OTHER PUBLICATIONS

Totaro, "Mitral valve repair for isolated prolapse of the anterior leaflet: an 11-year follow-up," European Journal of Cardio-thoracic Surgery, 15:119-126 (1999).
Uchida et al., "Percutaneous Cardiomyotomy and Valvulotomy with Angioscopic Guidance," Am. Heart J., pp. 121:1221-1224 (1991).
Umana et al., "'Bow-tie' Mitral Valve Repair Successfully Addresses Subvalvular Dysfunction in Ischemic Mitral Regurgitation," Surgical Forum, XLVIII:279-280 (1997).
Umana et al., "Bow-Tie" Mitral Valve Repair: An Adjuvant Technique for Ischemic Mitral Regurgitation, Ann. Thorac. Surg., 66:1640-1646 (1998).
Votta et al., "3-D Computational Analysis of the Stress Distribution on the Leaflets after Edge-to-Edge Repair of Mitral Regurgitation," Journal of Heart Valve Disease, 11:810-822 (2002).

LONG ARM VALVE REPAIR CLIP

CROSS-REFERENCE TO RELATED APPLICATIONS

This application claims the benefit of U.S. Provisional Patent Application No. 62/505,810, filed May 12, 2017, which is incorporated herein by reference in its entirety.

BACKGROUND

Field of Disclosed Subject Matter

The disclosed subject matter is directed to medical devices for the endovascular, percutaneous or minimally invasive surgical treatment of bodily tissues, such as tissue approximation or valve repair. More particularly, the present invention relates to repair of valves of the heart and venous valves.

Surgical repair of bodily tissues can involve tissue approximation and fastening of such tissues in the approximated arrangement. When repairing valves, tissue approximation includes coapting the leaflets of the valves in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall can be damaged or otherwise dysfunctional. Commonly, the valve annulus can be damaged, dilated, or weakened limiting the ability of the mitral valve to close adequately against the high pressures of the left ventricle.

Description of Related Art

Treatments for mitral valve regurgitation rely on valve replacement or repair including leaflet and annulus remodeling, the latter generally referred to as valve annuloplasty. Another technique for mitral valve repair, which relies on suturing adjacent segments of the opposed valve leaflets together is referred to as the "bow-tie" or "edge-to-edge" technique. Devices, and systems should preferably not require open chest access and be capable of being performed either endovascularly, i.e., using devices, such as a catheter, which are advanced to the heart from a point in the patient's vasculature remote from the heart. Preferably, such devices and systems allow for repositioning and optional removal of a fixation device (i.e., valve repair clip) prior to fixation to ensure optimal placement. Such devices and systems likewise can be useful for repair of tissues in the body other than heart valves.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a fixation device for treating a patient.

In accordance with the disclosed subject matter, a fixation device for engaging tissue includes a pair of fixation elements, each fixation element has a first end and a second end opposite the first end, the first ends are moveable between a closed position and an open position. The fixation device further includes a pair of gripping elements. Each gripping element is moveable with a respective fixation element and disposed in opposition to at least a portion of the respective fixation element to capture tissue therebetween. The fixation device further includes a central portion operatively connected to each gripping element at a respective central portion-gripping element interface. The central portion has a distal end and a width "$W_1$" proximate the distal end. Each gripping element has a free end opposite its respective central portion-gripping element interface and a length "$L_1$" defined between the respective central portion-gripping element interface and the free end. The length $L_1$ fixation elements is at least about three times the width $W_1$.

The ratio of the width to the length $W_1:L_1$ can be about 1:3. The distal end can define a reference plane perpendicular to a central axis of the central portion and wherein a height "$H_1$" can be defined by a vertical dimension between the reference plane and the central portion-gripping element interfaces. The ratio of the height to the length $H_1:L_1$ can be about 1:1.8. The length $L_1$ can be about 0.35 inches. The central portion can have a generally U-shaped configuration with the distal end disposed between the respective central portion-gripping element interfaces. Each fixation element can be rotatable about a respective axis point, and each fixation element can have an elongate portion defining a respective reference axis. A length "$L_2$" can be defined along the respective reference axis between the respective axis point and the respective second end of each fixation element. The length $L_2$ can be at least the length of $L_1$. The ratio of the lengths $L_2:L_1$ can be about 1.35:1. Each gripping element can have a plurality of rows of fixation elements. For example, each gripping element can nave at least four rows of friction elements extending from a gripping element surface. Each row can include one or more friction elements.

In accordance with the disclosed subject matter, a fixation device for engaging tissue can include a pair of fixation elements, each fixation element having a first end and a second end opposite the first end, the first ends being moveable (e.g., translating and/or rotating) between a closed position and an open position. The fixation device can further include a pair of gripping elements, each gripping element being moveable with a respective fixation element and disposed in opposition to at least a portion of the respective fixation element to capture tissue therebetween. The fixation device can further include a central portion operatively connected to each gripping element at a respective central portion-gripping element interface. The central portion can have a distal end defining a reference plane perpendicular to a central axis of the central portion. The central portion can have a width "$W_1$" proximate the distal end, each gripping element having a free end opposite its respective central portion-gripping element interface. A length "$L_1$" can be defined between the respective central portion-gripping element interface and the free end. A height "$H_1$" can be defined by a vertical dimension between the reference plane and the central portion-gripping element interfaces. The length $L_1$ can be at least 1.8 times the height $H_1$.

The ratio of the height to the length $H_1:L_1$ can be about 1:1.8. The ratio of the width to the length $W_1:L_1$ can be about 1:3. The length $L_1$ can be about 0.35 inches. The central portion can have a generally U-shaped configuration with the distal end disposed between the respective central portion-gripping element interfaces. Each fixation element can be rotatable about a respective axis point, each fixation element can have an elongate portion defining a respective reference axis. A length "$L_2$" can be defined along the respective reference axis between the respective axis point and the respective second end of each fixation element. The length $L_2$ can be at least the length of $L_1$. The ratio of the lengths $L_2:L_1$ can be about 1.35:1. Each gripping element can have at least four rows of friction elements extending from a gripping element surface. Each row can include one or more friction elements.

DETAILED DESCRIPTION

Figure 1:
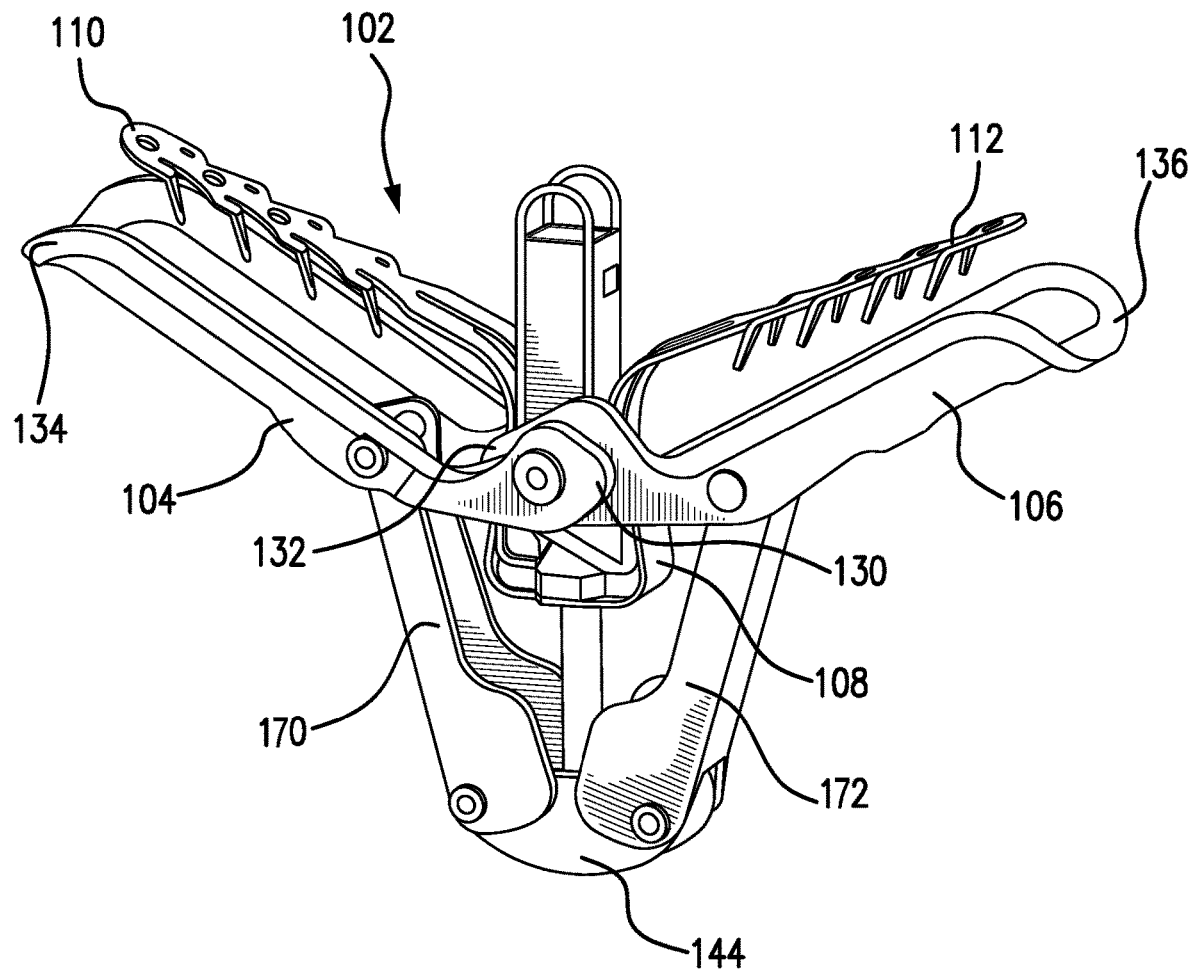
FIG. 1 is a perspective view of an exemplary embodiment a fixation device in accordance with the disclosed subject matter.

Reference will now be made in detail to the various exemplary embodiments of the disclosed subject matter, exemplary embodiments of which are illustrated in the accompanying drawings.

The device of the disclosed subject matter provides an edge-to-edge transcatheter valve repair option for patients having various conditions, including regurgitant mitral valves or tricuspid valves. In grasping tissue and leaflet capture for mitral valve disease, there are occasions where a particularly challenging anatomy can be associated with larger dynamic gaps between leaflet tips that cannot be effectively captured by previous designs. In order to improve ease of achieving procedural success in these cases, a fixation device (i.e., valve repair clip) having modified fixation elements and gripping elements is disclosed herein. The fixation device disclosed herein is able to bridge larger gaps in functional mitral regurgitation (FMR) while also providing more reliable leaflet capture in cases of dynamic, chaotic, or overly severe degenerative mitral regurgitation (DMR), such as in cases of Barlow's Syndrome.

The device of the disclosed subject matter herein can provide for an edge-to-edge valve repair option for degenerative mitral valve regurgitation (DMR) and functional mitral valve regurgitation (FMR) cases. In addition, the device of the disclosed subject matter can be used in tricuspid valve treatments.

To address various problems associated with treating severely diseased tricuspid valve anatomies, a fixation device is disclosed herein with improved configurations for enhanced performance.

Generally, and as set forth in greater detail below, the disclosed subject matter provided herein includes a fixation device for engaging tissue including a pair of fixation elements, each fixation element has a first end and a second end opposite the first end, the first ends are moveable between a closed position and an open position. The fixation device further includes a pair of gripping elements. Each gripping element is moveable with respect to a respective fixation element and disposed in opposition to at least a portion of the respective fixation element to capture tissue therebetween. The fixation device further includes a central portion operatively connected to each gripping element at a respective central portion-gripping element interface. The central portion has a distal end and a width "$W_1$" proximate the distal end. Each gripping element has a free end opposite its respective central portion-gripping element interface and a length "$L_1$" defined between the respective central portion-gripping element interface and the free end. The length $L_1$ of the fixation elements is at least about three times the width $W_1$. Additionally, or alternatively, and in accordance with another aspect of the disclosed subject matter the distal end of the central portion can define a reference plane perpendicular to a central axis of the central portion wherein, a height "$H_1$" can be defined by a vertical dimension between the reference plane and the central portion-gripping element interfaces, and the length $L_1$ can be at least 1.8 times the height $H_1$.

Figure 2:
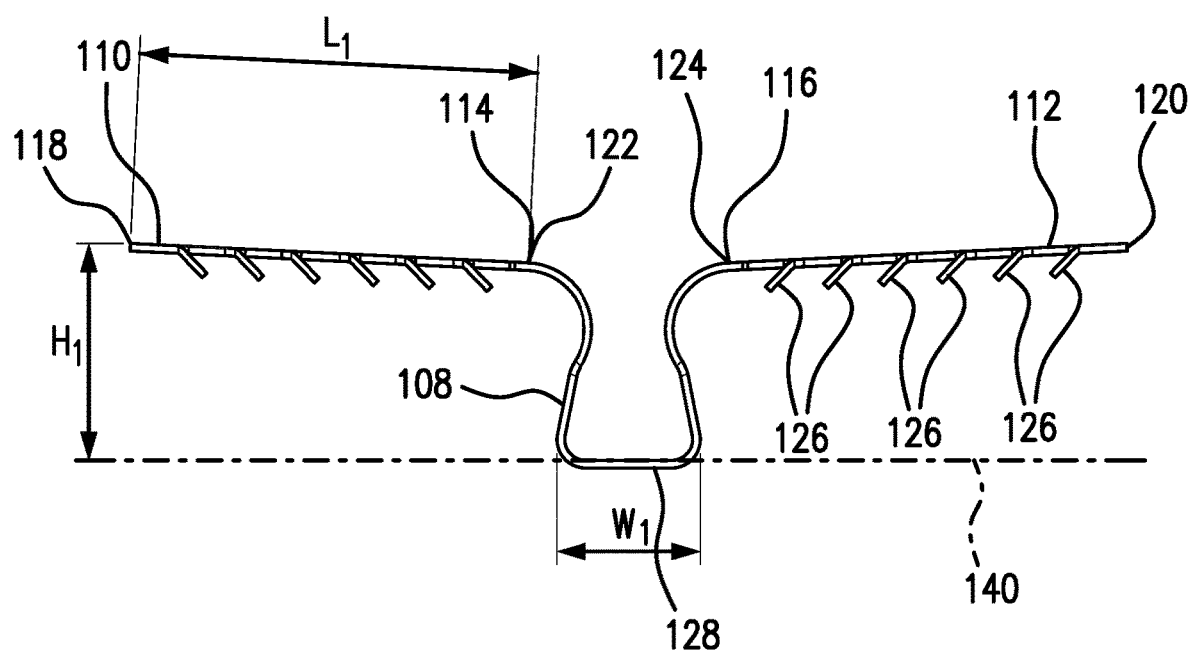
FIG. 2 is a front view of a pair of gripping elements and a central portion therebetween.
Figure 3:
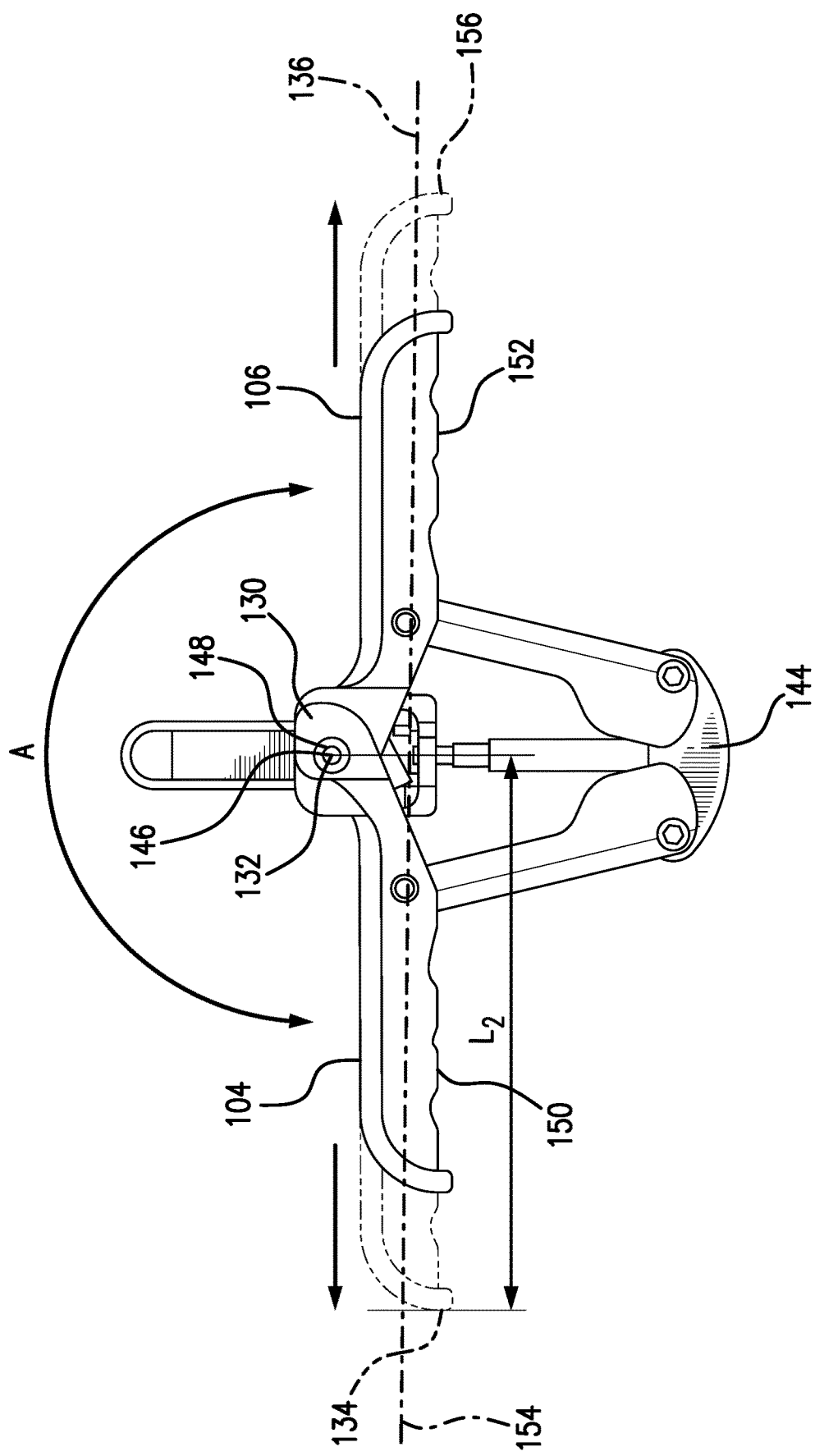
FIG. 3 is a front view of a portion of the fixation device of FIG. 1.
Figure 9A:
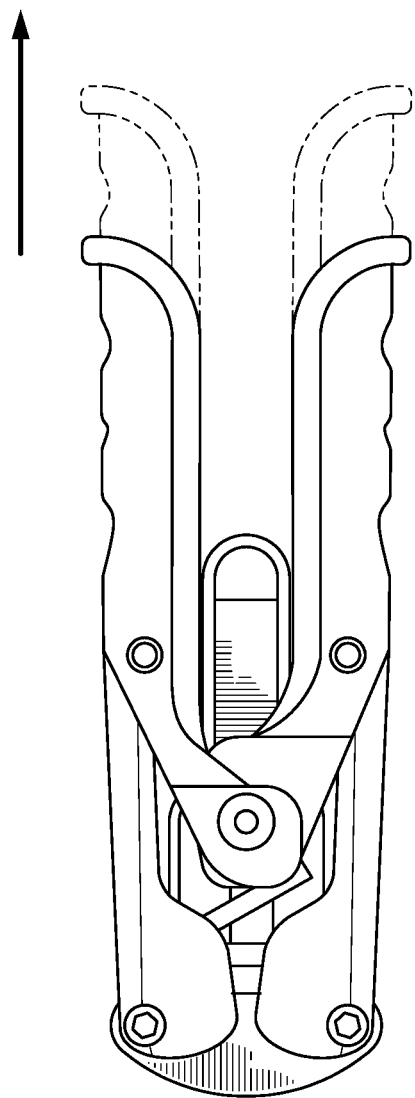
FIGS. 9A-9C are front views of a portion of the fixation device of FIG. 1 at various positions.

Referring to FIGS. 1-3 for the purpose of illustration and not limitation, a fixation device 102 for engaging tissue is disclosed herein and includes a pair of fixation elements 104, 106 each having a first end 130, 132 and a second end 134, 136 opposite the first end, the first ends 130, 132 being movably coupled together such that the fixation elements are moveable between a closed position and an open position. For the purpose of illustration and not limitation an exemplary embodiment of a closed position is shown in FIG. 9A and an exemplary embodiment of an open position is shown in FIG. 9C.

As embodied herein, and in accordance with the disclosed subject matter, the fixation device further includes a pair of gripping elements 110, 112, each gripping element moveable with a respective fixation element 104, 106, and disposed in opposition to at least a portion of the respective fixation element to capture tissue therebetween. The fixation device further includes a central portion 108 operatively connected to each of the gripping elements 110, 112 at respective central portion-gripping element interface 122, 124. With reference to FIG. 2, the central portion 108 has a distal end 128 and a width "$W_1$" proximate the distal end. Each gripping element has a free end 118, 120 opposite its respective central portion-gripping element interface 122, 124, wherein a length "$L_1$" is defined between the respective central portion-gripping element interface 122, 124 and the free end 118, 120. As disclosed herein, the length $L_1$ is at least about three times the width $W_1$. The ratio of the width to the length $W_1:L_1$ can be about 1:3

In accordance with another aspect of the disclosed subject matter, the distal end can define a reference plane 140 perpendicular to a central axis of the central portion. A height "$H_1$" can be defined by a vertical dimension between the reference plane 140 and the central portion-gripping element interfaces 122, 124. For example, the length $L_1$ can be at least 1.8 times the height $H_1$. Thus, the ratio of the height to the length $H_1:L_1$ can be about 1:1.8. The length $L_1$ can be about 0.35 inches.

The central portion 108 can be a than each of the gripper elements or can be formed integrally as a single piece with the gripper elements as embodied herein. For example, the central portion can have a generally U-shaped configuration with the distal end 128 disposed between the central portion-gripping element interfaces 122,124. As embodied herein for the purpose of illustration and not limitation, the central portion 108 can be connected to the gripping elements. However, the central portion is not limited to a U-shaped configuration and can be a component having any number of shapes, sizes, and functions.

Figure 4A:
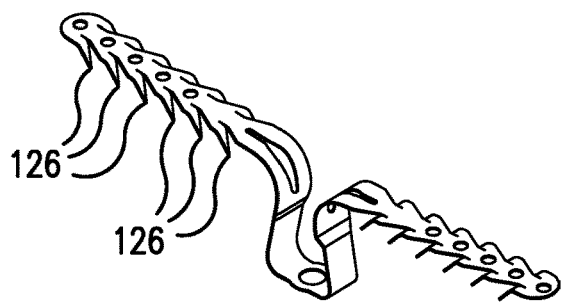
FIGS. 4A-4D are perspective views of a various embodiments of the gripping elements.
Figure 4B:
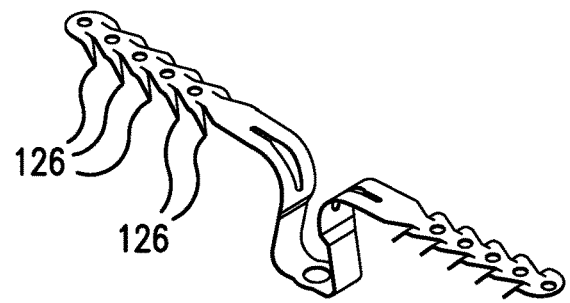

Further in accordance with the disclosed subject matter each gripper element can include one or more friction elements. As embodied herein, each gripping element includes a plurality of friction elements, such as in rows. Referring now to FIGS. 4 and 5 for the purpose of illustration and not limitation, various exemplary embodiments of the friction elements 126 are provided. As depicted, a plurality of friction elements 126 can be provided. For example, each gripping element 110, 112 can have at least four rows of friction elements 126 extending from a gripping element surface. Each row can include one or more friction elements 126. For the purpose of illustration and not limitation, FIG. 4A shows six rows of friction elements 126 and FIG. 4B shows five rows of friction elements. Six rows of friction elements 126 on either side of the gripping element (12 total), can allow for improved tissue engagement during leaflet capture. This gripping element design increases the assurance that single device leaflet attachment (SLDA) will not occur during a procedure, which constitutes an adverse safety risk. If the fixation device requires adjustment after an initial leaflet capture, the fixation elements can be opened, the gripping element can be raised vertically, and tissue can disengage from the fixation device, facilitating re-grasp and capture.

Figure 4C:
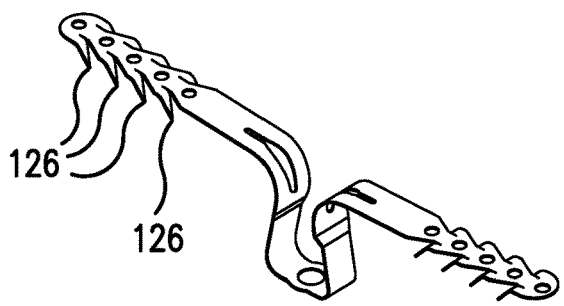
Figure 4D:
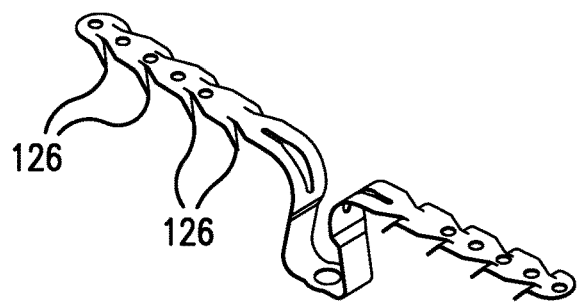
Figure 5:
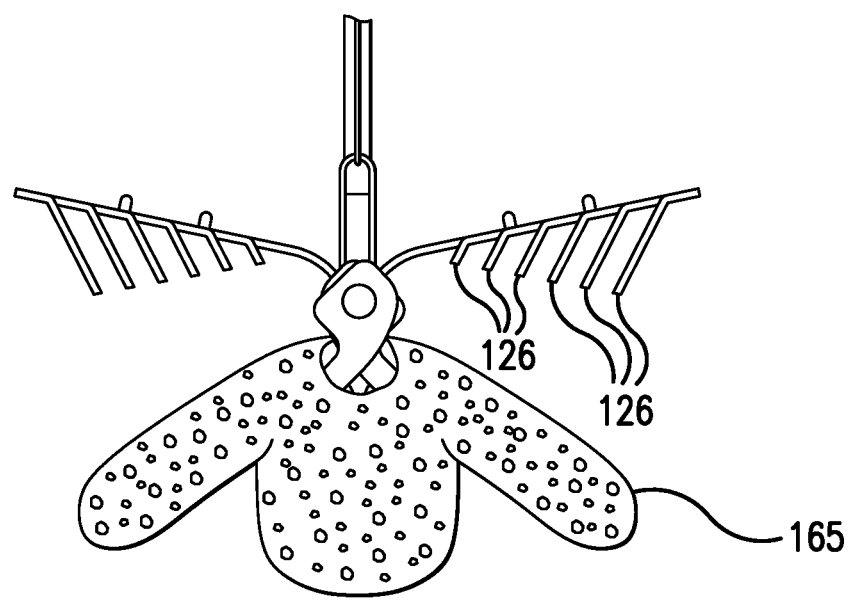
FIG. 5 is a front view of a modified embodiment of the fixation device of FIG. 1.

Alternatively, each gripping element can have fewer rows of friction elements as appropriate, such as 1 row, 2 rows, 3 row, or 4 rows, as shown in FIGS. 4C and 4D. Fewer rows can improve the ability of the device to release tissue during adjustment after an initial leaflet capture. In comparing FIGS. 4A-4C, in decreasing order, tissue engagement is expected to be highest in FIG. 4A, then FIG. 4B, then FIG. 4C, and in decreasing order, ease of leaflet release is expected to be highest in FIG. 4C, the FIG. 4B, then FIG. 4A.

Friction elements can be distributed near the free ends of the gripping elements 118, 120, as shown in FIGS. 4B and 5B, or the rows can be redistributed along the length of the gripping element, as shown in FIG. 4D. The redistributed rows can provide an alternate performance compromise between leaflet engagement and leaflet release. Spacing of gripping elements may be biased (non-uniform) to provide performance improvements in either leaflet capture, leaflet release, or both.

The length of each friction element 126 can be constant, as shown in FIGS. 1, 2 and 4. Alternatively, the friction elements 126 can be provided with varying sizes. For example, the length can increase in length toward the free ends of the gripping elements 118, 120, as shown in FIG. 5. The increase in length can be linear or parabolic. The variation in length as shown for FIG. 5C is for purpose of illustration not limitation, and the variation in length can be significantly smaller than shown. This length variation may be continuous or staggered in alternating rows of gripping elements to produce an undulating profile.

Figure 6:
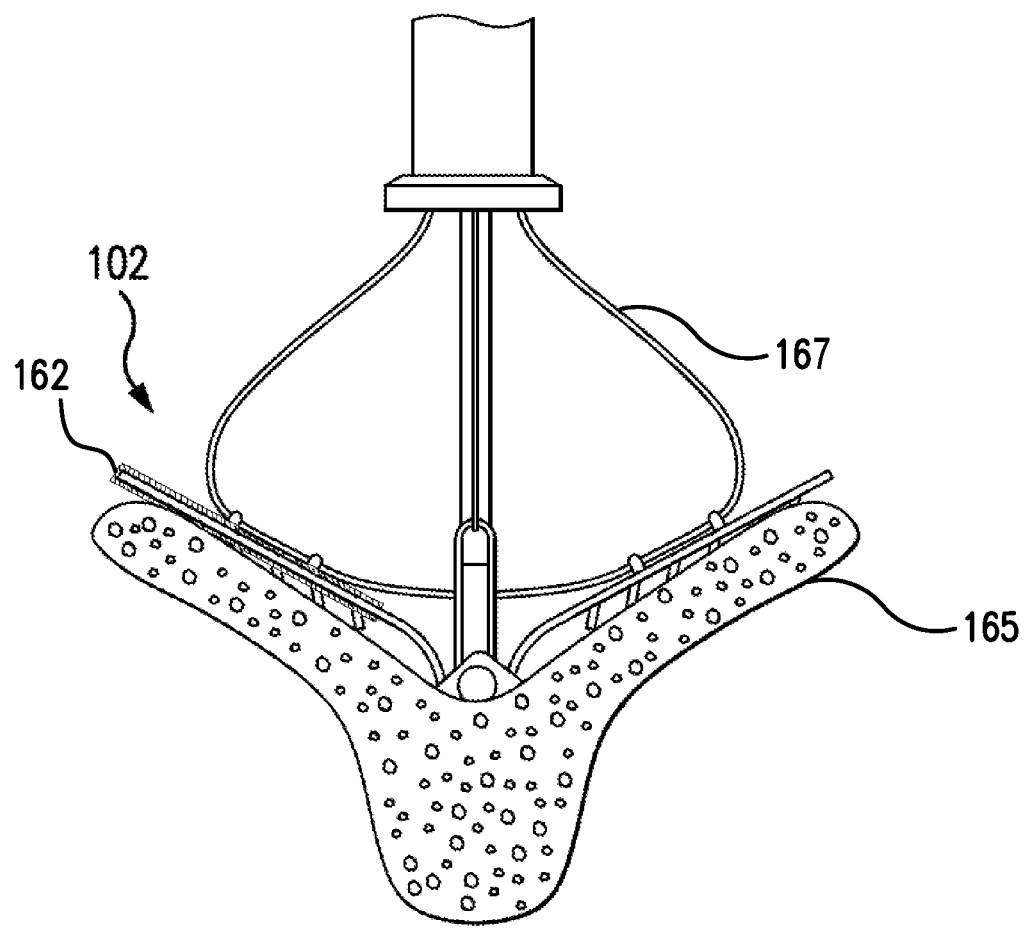
FIG. 6 is a front view of an embodiment of the fixation device of FIG. 1 on the distal end of a catheter.

Referring now to FIG. 6, the fixation device can have a cover over the gripping elements. The cover can be made of a variety of suitable materials. For purpose of comparison only, a cover 162 is shown on only one gripping element in FIG. 6 whereas the other gripping element is depicted without a cover. However, each gripping element can have a cover 162. The cover can be configured for friction elements 126 to protrude at varying degrees along the length of the gripping elements 110, 112. For example, the friction elements can have a linearly or parabolically increasing protruded length when moving toward the free ends by varying the gripping element cover dimensions. The cover 162 can cover the gripping element friction elements 126 such that only a portion of the friction elements 126 protrudes through the cover. Increased friction element height protruding through the cover can enhanced tissue fixation. The height can be varied along the length of the gripping element flat section such that tissue fixation is maximized proximate the free end of the gripping element minimized proximate the first end of the gripper. For example, the cover could be a type of film with a varied thickness along the length of the gripping element. The cover 162 can form a rectangular sheath around the gripper elements so only part of the friction element length protrudes through the cover thickness. This configuration can increase the combination of reliable leaflet capture and the leaflet release. As further depicted in FIG. 6, a cover 165 can also be provided over the fixation elements 104, 106. The cover 165 can be made of polyester fabric.

Further in accordance with the disclosed subject matter, the fixation elements also can be provided with increased length as compared to conventional fixation devices. The fixation device can further include a base 144 operatively connected to the fixation elements. Each fixation element 134, 136 can be rotatable about a respective axis point 146, 148. Each fixation element 134, 136 can have an elongate portion 150, 152 defining a respective reference axis 134, 136. A length "$L_2$" can be defined along the respective reference axis 154, 156 between the respective axis point 146, 148 and the respective second end 134, 136 of each fixation element. For purpose of discussion and comparison with a conventional device having a shorter length fixation element, the increased length of each fixation element of the disclosed subject matter is depicted in dashed lines in FIG. 3 as well as FIGS. 9A-9C. The length $L_2$ of the fixation element can be at least about the length of $L_1$. For example, the ratio of the lengths $L_2:L_1$ can be about 1.35:1. For purpose of comparison, FIGS. 7 and 8 depict the fixation elements of the disclosed subject matter labeled as embodiment "A" whereas a conventional fixation device is depicted as embodiment "B."

Figure 7:
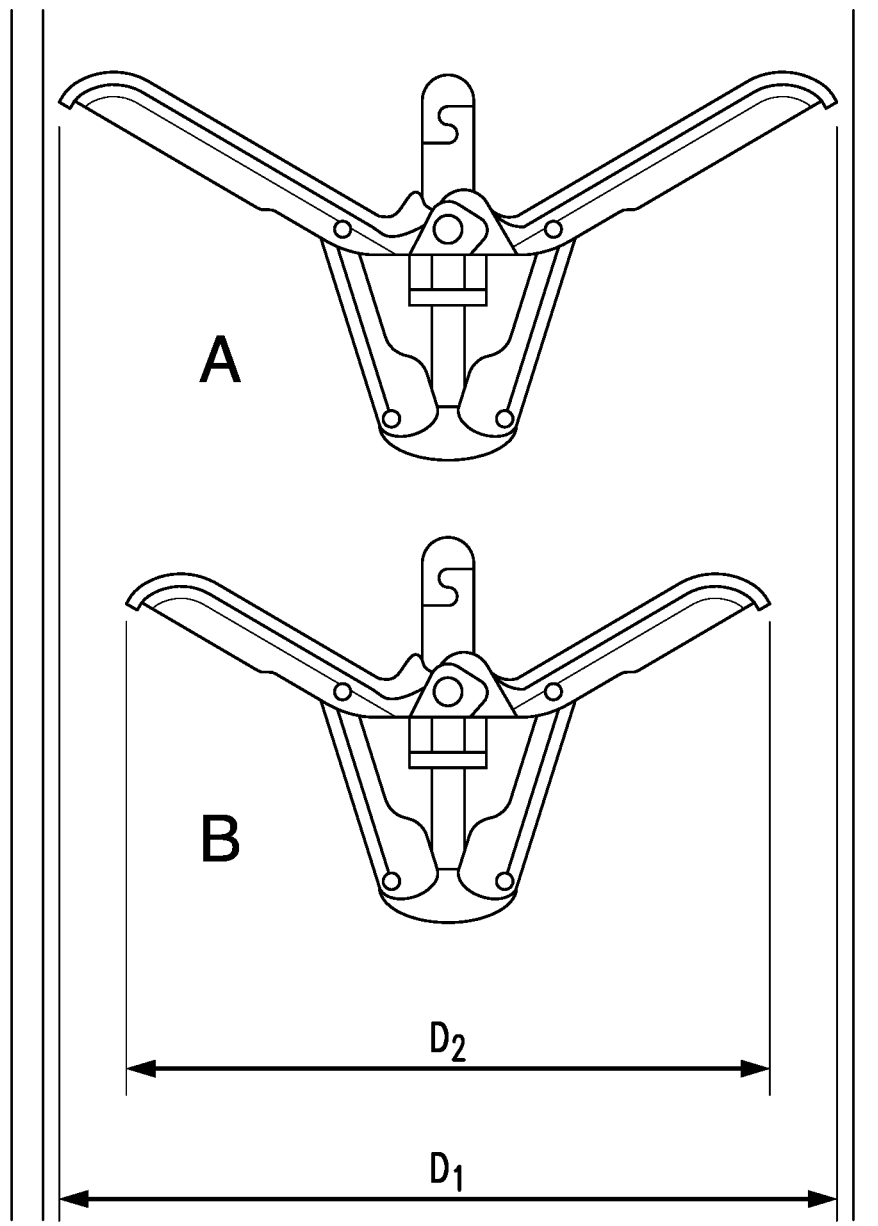
FIG. 7 is a comparative front view of a portion of the fixation device of FIG. 1.
Figure 8:
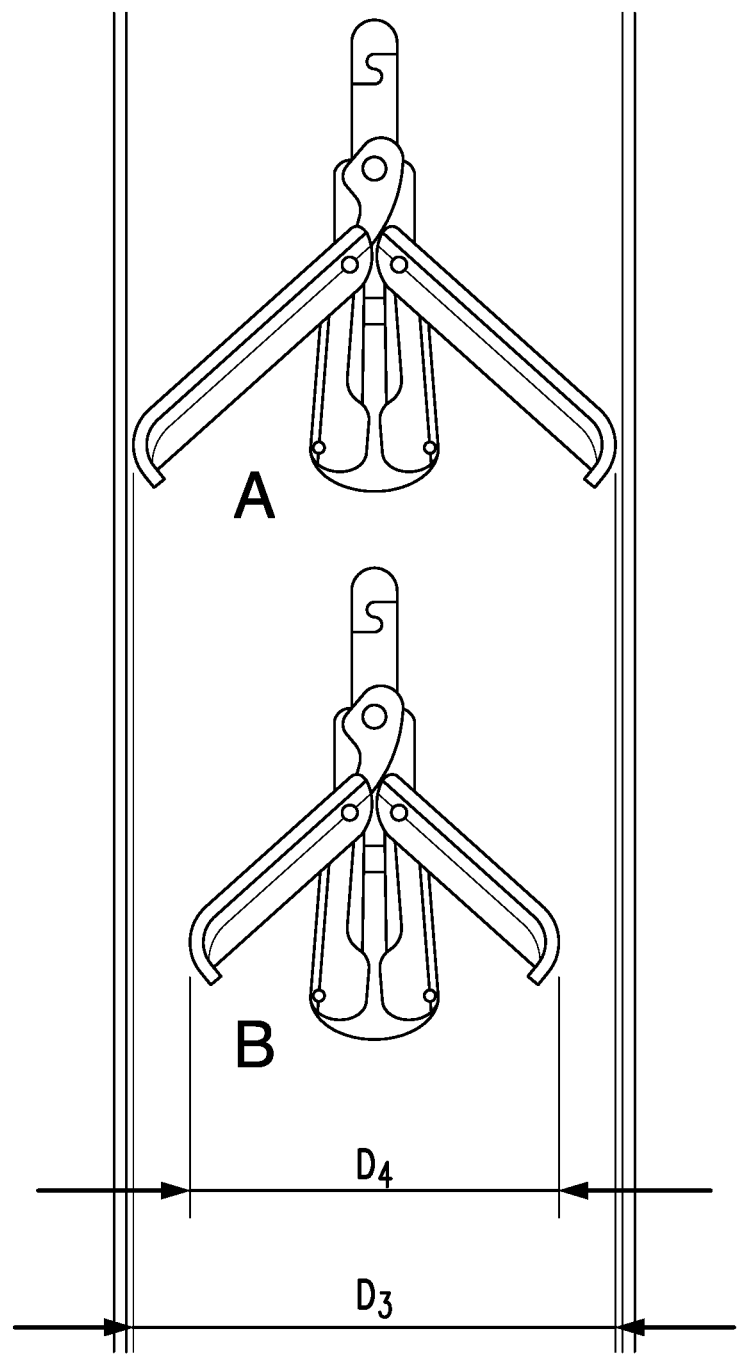
FIG. 8 is a comparative front view of a portion of the fixation device of FIG. 1.

In FIG. 7, the fixation devices are in an open position, wherein tissue capture can occur in this position. A dimension can be defined as the horizontal distance between the second ends of the fixation elements 134, 136. For embodiment A, dimension $D_1$ can be about 24 millimeters, whereas for embodiment B, dimension $D_2$ can be about 19 millimeters. In FIG. 8, the fixation elements are in an inverted position, wherein tissue release and device retraction can occur in this position. For embodiment A, dimension $D_3$ can be about 15 millimeters, whereas for embodiment B, dimension $D_4$ can be about 11 millimeters.

Figure 9B:
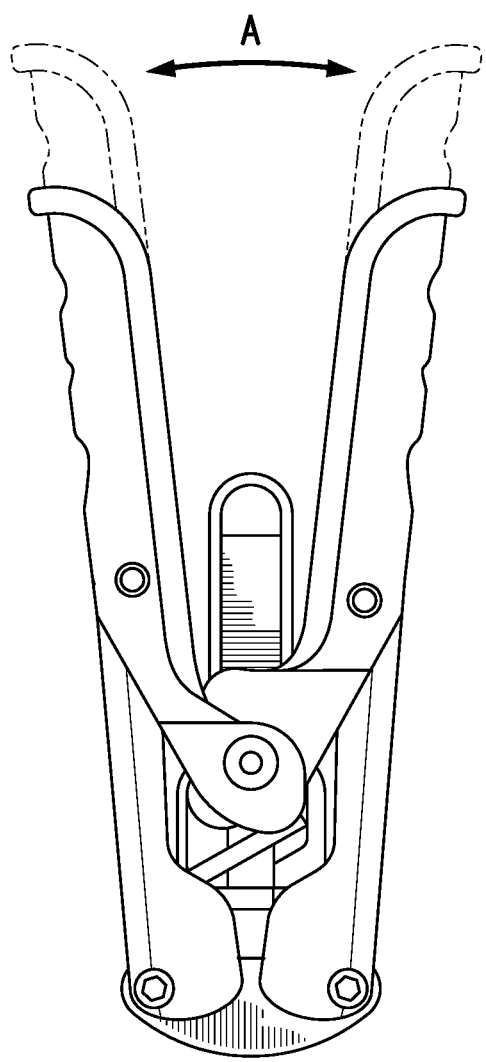
Figure 9C:
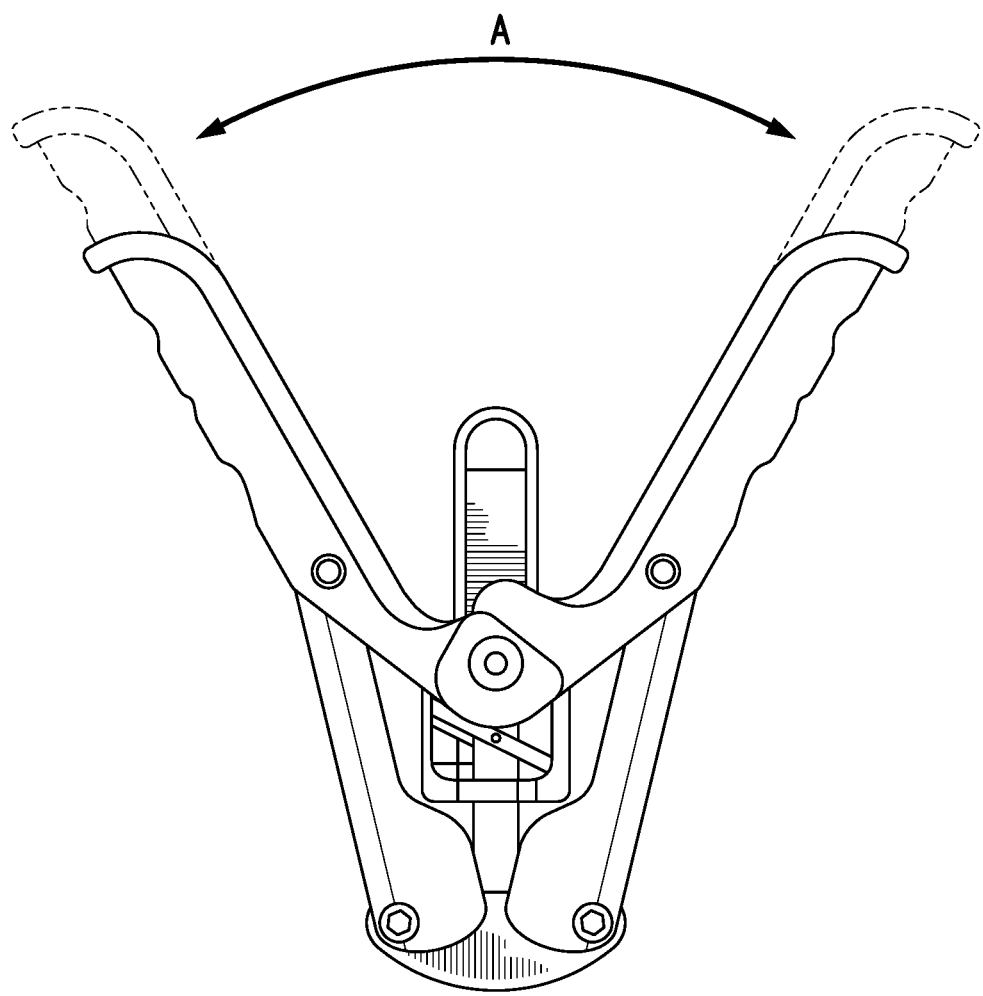

Referring now to FIGS. 9A-C, various positions of the fixation device 102 are depicted for purpose of illustration and not limitation. Elongated fixation elements of the disclosed subject matter are illustrated in dashed lines for comparison to shorter fixation elements. In FIG. 9A the fixation device is in the closed position, wherein the fixation elements are positioned vertically. FIGS. 9B and 9C illustrate the fixation elements positioned with an angle A between the two elements. In FIG. 9B, A is 10 degrees and in FIG. 9C A is 60 degrees.

Figure 10:
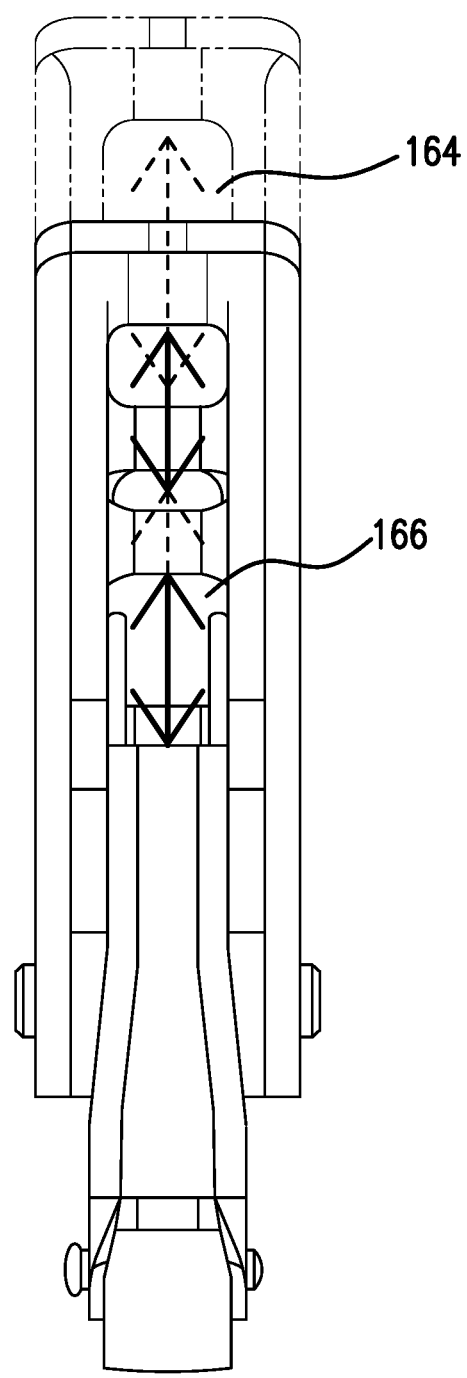
FIG. 10 is a side view of a fixation element of the fixation device of FIG. 1.
Figure 11A:
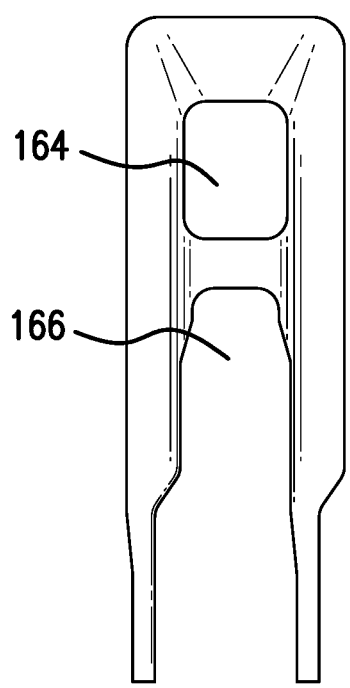
FIGS. 11A-11B are comparative side views of a fixation element of the fixation device of FIG. 1.
Figure 11B:
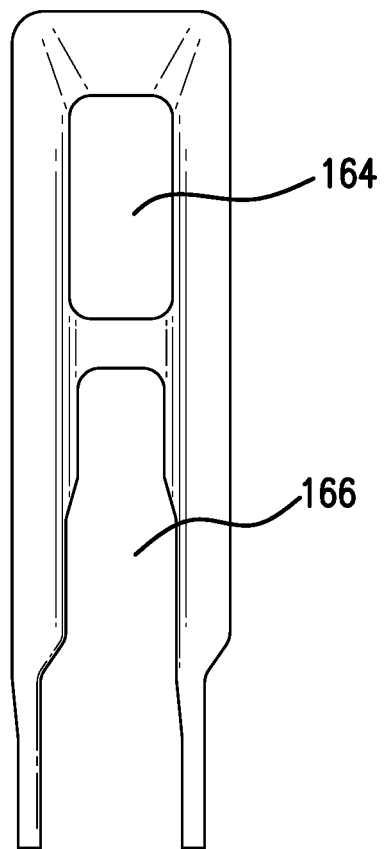

Referring now to FIGS. 10 and 11, side views of the fixation elements are shown wherein a first opening 164 and a second opening 166 have an increased length in an elongated fixation element of the disclosed subject matter, as compared to a shorter fixation element. In FIG. 10, arrows illustrate increased length of the openings 164, 166, while their respective widths remain constant. Similarly, FIG. 11B illustrates the increased length of the first and second openings 164, 166, as compared to the shorter fixation element in FIG. 11A.

Figure 12A:
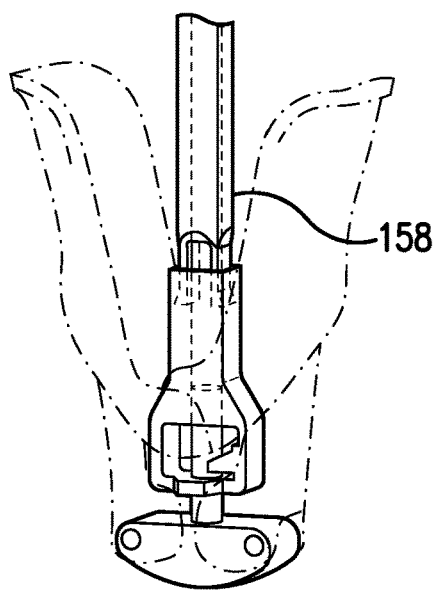
FIG. 12A is a perspective view of a L-Lock component in combination with the fixation device of FIG. 1.
Figure 12B:
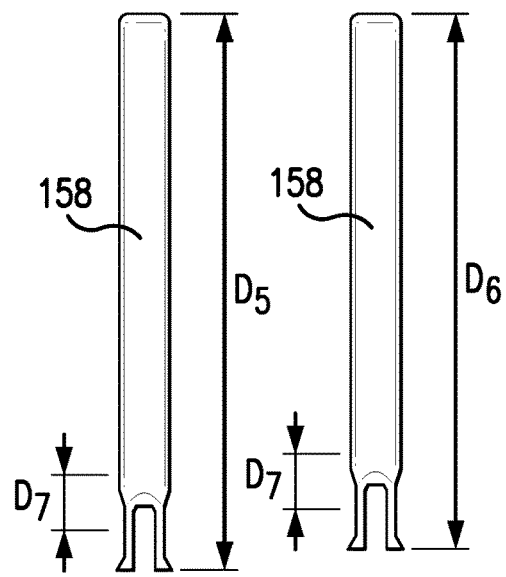
FIG. 12B is a front view of the L-Lock component.
Figure 12C:
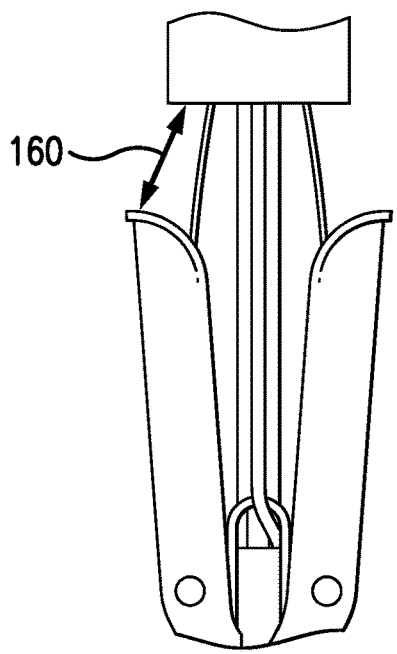
FIG. 12C is a front view of an embodiment of the fixation device of FIG. 1 on the distal end of a catheter.

Referring now to FIGS. 12A-C, a portion of a system used to deliver the fixation device 102 to the desired position within body can include an L-Lock component 158, as shown in FIG. 12A. The L-Lock component can be elongated to accommodate the elongated fixation element 102 of the disclosed subject matter. For example, the length of the L-Lock can be increased from a dimension $D_6$ to a dimension $D_5$ to accommodate an elongated fixation device of the disclosed subject matter. For example, $D_6$ can be about 0.52 inches and $D_5$ can be about 0.56 inches. A U-shaped portion of the L-Lock can be the same dimension for both the shorter and elongated L-Lock, as shown by $D_7$. The elongated L-Lock thus can extend the fixation device 102 an increased distance from a distal end of the catheter to keep a gap 160 when the fixation elements are elongated. This can improve tissue clearance during the procedure.

To accommodate thicker leaflets when elongated fixation elements are present on the fixation device design, a longer L-Lock deployment mechanism may also be required to avoid any leaflet pinching against the radiopaque ring on the tip of the device delivery catheter. Leaflet thicknesses is typically below 2 mm, but may exceed this in cases of myxotamous disease. Therefore, this potential "gap" accommodation can be required in cases where thicker leaflets are anticipated.

Figure 13:
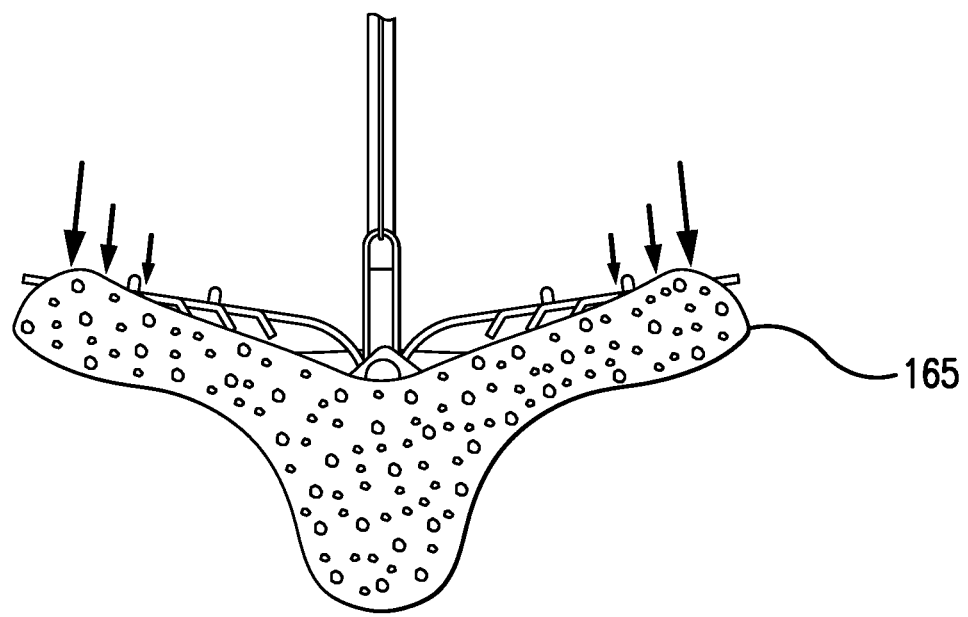
FIG. 13 is a front view of an embodiment of the fixation device of FIG. 1.

Referring now to FIG. 13, when gripping elements 110 and 112 are lowered toward respective fixation elements 104, 106 for tissue capture, the fixation elements and gripping elements can misfit by a 60-degree interference angle such that tissue can be pinched more immediately, completely, and forcefully at the free ends of the gripping elements. The arrows in FIG. 13 illustrate the larger amount of force that can be placed on tissue towards the free ends of the gripping elements. This engagement, which appears to be a mis-fitting and non-parallel assembly, provides a more secure fixation during fixation element closure and increases the likelihood that leaflets will not be released as the fixation device moves towards the closed position.

Figure 14:
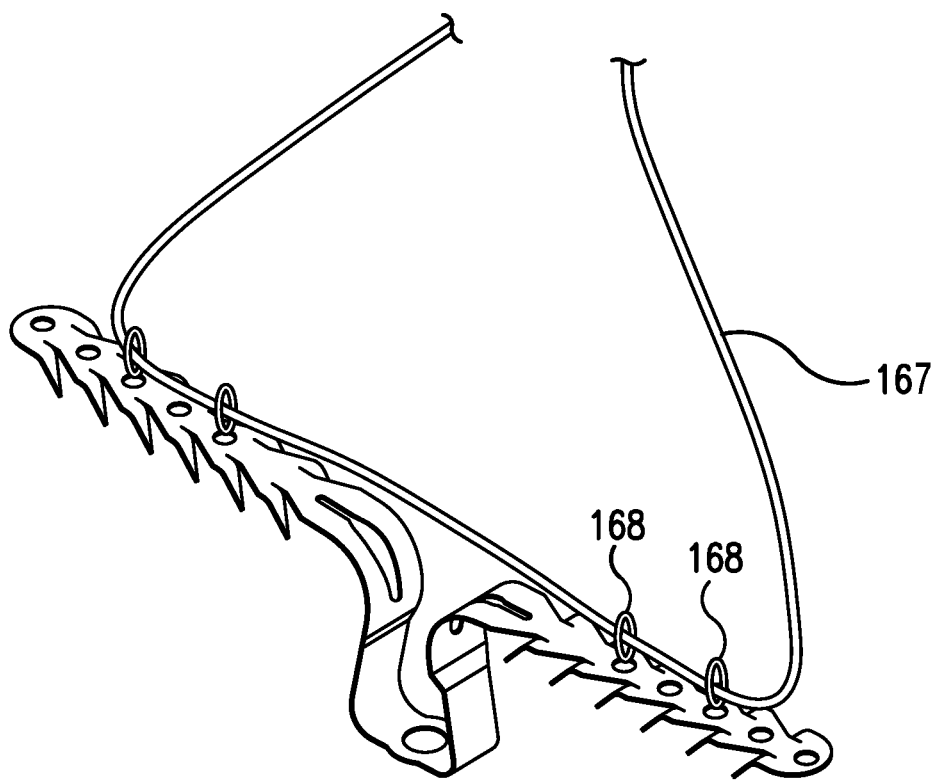
FIG. 14 is a perspective view of an embodiment of the gripping element of FIG. 2.

Referring now to FIG. 14, the gripping elements of the disclosed subject matter can each include more than one suture loop 168. As shown in FIG. 14 for purpose of illustration and not limitation, each gripping element can include two suture loops 168. The suture loops can be used in combination with sutures to raise and lower the gripping elements.

Additional details of suitable components and operation thereof along with related features are set forth in U.S. Pat. No. 7,226,467 to Lucatero et al., U.S. Pat. No. 7,563,267 to Goldfarb et al., U.S. Pat. No. 7,655,015 to Goldfarb et al., U.S. Pat. No. 7,736,388 to Goldfarb et al., U.S. Pat. No. 7,811,296 to Goldfarb et al., U.S. Pat. No. 8,057,493 to Goldfarb et al., U.S. Pat. No. 8,303,608 to Goldfarb et al., U.S. Pat. No. 8,500,761 to Goldfarb et al., U.S. Pat. No. 8,734,505 to Goldfarb et al., U.S. Pat. No. 8,740,920 to Goldfarb et al., U.S. Pat. No. 9,510,829 to Goldfarb et al., U.S. Patent Publication No. 2007/0197858 to Goldfarb et. Al, U.S. Patent Application Publication No. 2017/0042546 to Goldfarb et al., and U.S. Patent Application Publication No. 2017/0239048 to Goldfarb et al., each of which is incorporated by reference in its entirety herein.

The fixation device of the disclosed subject matter with gripper elements of greater length $L_1$ relative to the width $W_1$ and/or height $H_1$ surprisingly improves the function of a single fixation device and reduces the need to require more than one fixation device to be implanted to sufficiently reduce a patient's valvular regurgitation. For this reason, a fixation device that more completely reduces mitral regurgitation (MR) is desired, and a reduced number of fixation devices.

In patients with severe FMR, large annulus dilatation is chronically present, which causes otherwise healthy leaflets to fail to coapt or seal during cardiac systole. As a result, mitral regurgitation occurs. In these cases, a large gap can occur between leaflets that can be difficult to bridge with a fixation device, even when opened to its maximum wingspan at 180 degrees opening angle. The fixation device disclosed herein addresses this need.

Likewise, in patients with severe DMR, chaotically flailing or prolapsing leaflets can be difficult to grasp or capture. In these cases, conventional fixation elements (e.g., clip arms) may not be long enough to fully stabilize the excessively mobile leaflets during grasping. The longer fixation elements of the disclosed subject matter adequately secures the leaflets for subsequent leaflet capture with the gripping element. In this way, the longer fixation elements disclosed herein can reduce the number of grasp and capture attempts required to achieve procedural success.

Also, when a fixation device is implanted in a regurgitant valve, a double orifice geometry is created. The fixation device disclosed herein therefore is configured to improve procedural success, without increasing the risk of obstruction due to the device. For the device disclosed herein, a computational model was used to evaluate the impact of the length of the fixation elements. In addition, the fixation element length was confirmed to be within the range of surgical such lengths described in literature for treating severe leaflet prolapse (Barlow's Syndrome), or within 1 cm in length.

The elongated fixation device of the disclosed subject matter, further can improve tissue compression load at increased tissue thickness. For example, the gripping elements can be made of Nitinol which can have a stable pinching force over thin or thick leaflets versus a standard metal. Indeed, if a thick or thin leaflet is pinched in the gripper, it experiences a comparable force with nitinol. This is beneficial in a variety of situations, including in cases where a very thin delicate leaflet is inserted into the clip, but is folded over itself near the tip. This situation has been observed beating heart testing. When the leaflet is very thin, it is more prone to tearing under a pinch force, however, if it is doubled up, a typical elastic-plastic gripper deflects more and exerts more force on the vulnerable tissue, which can lead to piercing or tearing. The risk of tissue damage is mitigated through the use of a nitinol gripper where the pinching force remains stable despite any difference in tissue thickness. Therefore, the nitinol gripper design can minimize the occurrence of inadvertent device detachment from tissue (acute, subacute or even chronic) in what is defined as an SLDA (Single Leaflet Device Attachment—i.e., one side has detached) event.

The embodiments of the disclosed subject matter can be varied to treat any specific version of mitral valve, tricuspid valve, or other valves required edge-to edge approximation. For instance, various design features can be made "gentler" (reduced height of friction elements) for the purpose of treating a patient known to have fibroelastic deficiency or minor calcification. Alternatively, a more aggressive friction element height can be provided to more efficiently treat a myxomatous valve known to have thicker and fibrotic leaflet structures infiltrated with extracellular matrix.

Each of the components of the fixation device of the disclosed subject matter can be made of any suitable material (e.g., plastic, composites, metal, etc.) and technique for its intended purpose. In addition to the specific embodiments claimed below, the disclosed subject matter is also directed to other embodiments having any other possible combination of the dependent features claimed below and those disclosed above. As such, the particular features disclosed herein can be combined with each other in other manners within the scope of the disclosed subject matter such that the disclosed subject matter should be recognized as also specifically directed to other embodiments having any other possible combinations. Thus, the description of specific embodiments of the disclosed subject matter has been presented for purposes of illustration and description. It is not intended to be exhaustive or to limit the disclosed subject matter to those embodiments disclosed.

For purpose of understanding the assembly and operation of the disclosed subject matter, FIGS. 2-14 illustrate embodiments of components the fixation device 102 of FIG. 1 including in various possible positions during introduction and placement of the device 102 within the body to perform a therapeutic procedure. For example, FIG. 9A illustrates an embodiment of a device in a closed position for delivery through a catheter. It may be appreciated that the catheter may take the form of a guide catheter or sheath. As embodied herein, fixation elements can include engagement surfaces, wherein the engagement surfaces are configured to engage tissue between the gripping elements and the engagement surface. As shown in FIG. 9A, in the closed position, the opposed pair of fixation elements 134 are positioned so that engagement surfaces face each other. Each fixation element 104, 106 can have a cupped or concave shape so that together the arms surround a portion of the fixation device 102 and optionally contact each other on opposite sides of the device. This provides a low profile for the fixation device 102 which is readily passable through the catheter and through any anatomical structures, such as the mitral valve. In addition, the fixation device can further include an actuation mechanism. The actuation mechanism can comprise two legs 68 which are each movably coupled to a base 144. The base 144 is operatively connected with actuator rod which is used to manipulate the fixation device 102. At least a portion of the actuator rod can be disposed within the catheter and the distal end can attach to a stud which in turn is attached to the base 144. In some embodiments, the stud is threaded so that the actuator rod attaches to the stud by a screw-type action. However, the actuator rod and stud may be joined by any mechanism which is releasable to allow the fixation device 102 to be detached from the catheter.

FIG. 1 illustrates the fixation elements 104, 106 in the open position. In the open position, the fixation elements 104, 106 are rotated so that the engagement surfaces face a first direction. Distal advancement of the actuator rod causes a mechanism to engage the fixation elements 104, 106 which begin to rotate around the first fixation element axis point 146 and the second fixation element axis point 148. Such rotation and movement of the fixation elements 146, 148 radially outward causes rotation of the legs 170, 172 about joints so that the legs are directly slightly outwards. The actuator rod can be advanced to any desired distance correlating to a desired separation of the fixation elements 104, 106. In the open position, engagement surfaces are disposed at an acute angle relative to a longitudinal center of the device, and are preferably at an angle of between 90 and 180 degrees relative to each other.

Gripping elements 110, 112 are typically biased outwardly towards the fixation elements 104, 106. The gripping elements 110, 112 can be moved inwardly toward the longitudinal center of the device and held with the aid of on or more sutures 167 which can be in the form of sutures, wires, nitinol wire, rods, cables, polymeric lines, or other suitable structures. The sutures 167 can be connected with the gripping elements by threading the sutures in a variety of ways. When the gripping elements 110, 112 have one or more suture loops, as shown in FIG. 14, the suture 167 can pass through the one or more loops on each gripping element and double back.

The embodiment illustrated herein are adapted for repair of the mitral valve using an antegrade approach from a patient's left atrium. The fixation device 102 is advanced through the mitral valve from the left atrium to the left ventricle. The distal fixation elements 104, 106 are oriented to be perpendicular to a line of coaptation and then positioned so that the fixation elements contact the ventricular surface of the valve leaflets, thereby grasping the leaflets. The gripping elements 110, 112 remain on the atrial side of the valve leaflets so that the leaflets lie between the gripping elements and the fixation elements. As embodied herein the gripping elements 110, 112 have friction elements 126, as shown in FIG. 2, such as barbs which are directed toward the fixation elements 104, 106. The friction elements 126 can be angled toward the respective gripping element first ends 114, 116. However, neither the gripping elements 110, 112 nor the friction elements 126 contact the leaflets at this time.

The fixation device 102 can be repeatedly manipulated to reposition the device so that the leaflets are properly contacted or grasped at a desired location. Repositioning is achieved with the fixation device in the open position. In some instances, regurgitation of the valve can also be checked while the device is in the open position. If regurgitation is not satisfactorily reduced, the device can be repositioned and regurgitation checked again until the desired results are achieved.

It can also be desired to invert the fixation device 102 to aid in the release of leaflets, repositioning, or removal of the fixation device 102. FIG. 8 illustrates the fixation elements in the inverted position. By further advancement of the actuator rod, the fixation elements can be further rotated so that engagement surfaces of the fixation elements 104, 106 face outwardly and second ends 134, 136 point distally, with each fixation element 110, 112 forming an obtuse angle relative to the central axis. The angle between fixation elements 110, 112 is preferably in the range of about 270 to 360 degrees. Further advancement of the actuator rod further rotates the fixation elements 104, 106 around axis point 146, 148. This rotation and movement of the fixation elements 104, 106 radially outward causes rotation of the legs about joints so that the legs are returned toward an initial position, generally parallel to each other. The actuator rod can be advanced to any desired distance correlating to a desired inversion of the fixation elements 104, 106. Thus, a relatively large space can be created between the elements for repositioning. In addition, the inverted position allows withdrawal of the fixation device across the valve while minimizing trauma to the leaflets. Engagement surfaces provide an atraumatic surface for deflecting tissue as the fixation device is retracted proximally. The engagement surface can be on a portion of the fixation device capable of independent movement from the friction elements. As such, It should be further noted that friction elements are angled slightly to reduce the risk that the friction elements will catch on or lacerate tissue as the fixation device is withdrawn.

Once the fixation device 14 has been positioned in a desired location relative to the valve leaflets, the leaflets can then be captured between the gripping elements 110, 112 and the fixation elements 104, 106. At this time, the gripping elements 110, 112 are lowered toward the fixation elements 134, 136 so that the leaflets are held therebetween. At any time, the gripping elements 110, 112 can be raised and the fixation elements 104, 106 adjusted or inverted to reposition the fixation device 102, if regurgitation is not sufficiently reduced.

After the leaflets have been captured between the gripping elements and fixation elements in a desired arrangement, the fixation elements can be locked to hold the leaflets in this position or the fixation device can be returned to or toward a closed position. FIG. 9A illustrates the fixation elements in the closed position wherein the leaflets (not shown) can be captured and coapted. This is achieved by retraction of the actuator rod proximally relative to so that the legs of the actuation mechanism apply an upwards force to the fixation elements, which in turn rotate the fixation elements so that the engagement surfaces again face one another. The released gripping elements 110, 112 which are biased outwardly toward fixation elements 104, 106 are concurrently urged inwardly by the fixation elements 104, 106. The fixation device can then be locked to hold the leaflets in this closed position.

The fixation device 102 can then be released from the catheter. As mentioned, the fixation device 102 is releasably coupleable to the catheter. FIGS. 12A-12B illustrate a portion of the coupling mechanism, L-Lock 158. The L-Lock can be used in conjunction with a threaded mechanism to uncouple the fixation device 102 from the catheter.

After detachment, the repair of the leaflets or tissue can be observed by non-invasive visualization techniques, such as echocardiography, to ensure the desired outcome. If the repair is not desired, the fixation device 14 can be retrieved such as by the use of the sutures 167 so as to reconnect the fixation device 102 with the catheter. If the repair is desired, the sutures 167 can be disconnected by releasing one end of each line at the proximal end of the catheter and the other end pulled to draw the free end of the suture distally through the catheter and through the engagement with the gripping elements 110, 112.

While the above described embodiments of the invention utilize a push-to-open, pull-to-close mechanism for opening and closing fixation elements 104, 106, it should be understood that a pull-to-open, push-to-close mechanism is equally possible.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A fixation device for engaging tissue comprising:
a pair of fixation elements, each fixation element having a first end and a second end opposite the first end, the first ends being moveable between a closed position and an open position;
a pair of gripping elements, each gripping element moveable with a respective fixation element and disposed in opposition to at least a portion of the respective fixation element to capture tissue therebetween; and
a central portion operatively connected to each gripping element at a respective central portion-gripping element interface, the central portion having a distal end, the central portion having a width "$W_1$" proximate the distal end, each gripping element having a free end opposite its respective central portion-gripping element interface and a length "$L_1$" defined between the respective central portion-gripping element interface and the free end, wherein the length $L_1$ is at least about three times the width $W_1$,
wherein each gripping element includes at least one gripper line attachment location disposed along the length $L_1$ of the gripping element with each attachment location spaced from the free end of the gripping element.

2. The fixation device of claim 1, wherein the ratio of the width to the length $W_1:L_1$ is about 1:3.

3. The fixation device of claim 1, wherein the distal end defines a reference plane perpendicular to a central axis of the central portion and wherein a height "$H_1$" is defined by a vertical dimension between the reference plane and the central portion-gripping element interfaces.

4. The fixation device of claim 3, wherein the ratio of the height to the length $H_1:L_1$ is about 1:1.8.

5. The fixation device of claim 1, wherein the length $L_1$ is about 0.35 inches.

6. The fixation device of claim 1, the central portion having a generally U-shaped configuration with the distal end disposed between the respective central portion-gripping element interfaces.

7. The fixation device of claim 1, wherein each fixation element is rotatable about a respective axis point, each fixation element having an elongate portion defining a respective reference axis, wherein a length "$L_2$" is defined along the respective reference axis between the respective axis point and the respective second end of each fixation element.

8. The fixation device of claim 7, wherein the length $L_2$ is at least the length of $L_1$.

9. The fixation device of claim 8, wherein the ratio of the lengths $L_2:L_1$ is about 1.35:1.

10. The fixation device of claim 1, each gripping element has at least four rows of friction elements extending from a gripping element surface.

11. The fixation device of claim 10, wherein each row includes at least one friction element.

12. A fixation device for engaging tissue comprising:
a pair of fixation elements, each fixation element having a first end and a second end opposite the first end, the first ends being moveable between a closed position and an open position;
a pair of gripping elements, each gripping element moveable with a respective fixation element and disposed in opposition to at least a portion of the respective fixation element to capture tissue therebetween; and
a central portion operatively connected to each gripping element at a respective central portion-gripping element interface, the central portion having a distal end defining a reference plane perpendicular to a central axis of the central portion, the central portion having a width "$W_1$" proximate the distal end, each gripping element having a free end opposite its respective central portion-gripping element interface and a length "$L_1$" defined between the respective central portion-gripping element interface and the free end, wherein a height "$H_1$" is defined by a vertical dimension between the reference plane and the central portion-gripping element interfaces, and the length $L_1$ is at least 1.8 times the height $H_1$,
wherein each gripping element includes at least one gripper line attachment location disposed along the length $L_1$ of the gripping element and each attachment location spaced from the free end of the gripping element.

13. The fixation device of claim 12, wherein the ratio of the height to the length $H_1:L_1$ is about 1:1.8.

14. The fixation device of claim 12, wherein the ratio of the width to the length $W_1:L_1$ is about 1:3.

15. The fixation device of claim 12, wherein the length $L_1$ is about 0.35 inches.

16. The fixation device of claim 12, the central portion having a generally U-shaped configuration with the distal end disposed between the respective central portion-gripping element interfaces.

17. The fixation device of claim 12, wherein each fixation element is rotatable about a respective axis point, each fixation element having an elongate portion defining a respective reference axis, wherein a length "$L_2$" is defined along the respective reference axis between the respective axis point and the respective second end of each fixation element.

18. The fixation device of claim 17, wherein the length $L_2$ is at least the length of $L_1$.

19. The fixation device of claim 18, wherein the ratio of the lengths $L_2:L_1$ is about 1.35:1.

20. The fixation device of claim 12, each gripping element has at least four rows of friction elements extending from a gripping element surface.

21. The fixation device of claim 20, wherein each row includes at least one friction element.

* * * * *